(12) United States Patent
Luboshitz et al.

(10) Patent No.: US 6,224,594 B1
(45) Date of Patent: May 1, 2001

(54) DEVICES FOR PASSIVE MOTION OF JOINTS UNDER TRACTION

(75) Inventors: Shmuel Luboshitz, Raanana; Avraham Shekalim, Nesher; Hadar Raz, Jordan Valley, all of (IL)

(73) Assignee: Rimlon Ltd., Nazareth Ilit (IL)

( * ) Notice: Subject to any disclaimer, the term of this patent is extended or adjusted under 35 U.S.C. 154(b) by 0 days.

(21) Appl. No.: 09/292,607

(22) Filed: Apr. 15, 1999

Related U.S. Application Data

(63) Continuation-in-part of application No. 08/948,362, filed on Oct. 10, 1997.

(30) Foreign Application Priority Data

Jul. 15, 1998 (WO) ........................................ WO 98/14748

(51) Int. Cl.[7] .................................................. A61B 17/58
(52) U.S. Cl. ............................................ 606/57; 606/105
(58) Field of Search ................................ 606/54, 55, 57, 606/58, 96, 97, 98, 105, 90; 408/72 R

(56) References Cited

U.S. PATENT DOCUMENTS

| | | | |
|---|---|---|---|
| 4,604,997 | * 8/1986 | De Bastiani et al. | 606/55 |
| 4,987,886 | 1/1991 | McDonald et al. . | |
| 5,100,403 | * 3/1992 | Hotchkiss et al. | 606/56 |
| 5,328,446 | 7/1994 | Bunnell et al. . | |
| 5,472,410 | 12/1995 | Hamersly . | |
| 5,630,431 | 5/1997 | Taylor . | |
| 5,775,334 | 7/1998 | Lamb et al. . | |
| 5,846,245 | * 12/1998 | McCarthy et al. | 606/105 |

\* cited by examiner

Primary Examiner—Michael H. Thaler
Assistant Examiner—Julian W. Woo
(74) Attorney, Agent, or Firm—Mark M. Friedman

(57) ABSTRACT

A device for generating passive motion of a joint while applying traction includes a proximal bracket for engaging at least one pin inserted into a bone proximal to the joint and a distal bracket for engaging at least one pin inserted into a bone distal to the joint. The device also includes a tension-hinge mechanism connecting between the proximal and distal brackets. The tension-hinge mechanism includes a hinge for permitting rotational movement of the distal bracket relative to the proximal bracket about a hinge axis. At least one of the proximal bracket and the distal bracket is implemented as a movable bracket slidingly mounted so as to be displaceable in a direction generally perpendicular to the hinge axis. The tension-hinge mechanism also includes a traction mechanism for applying roughly constant force over a predefined range of positions of the movable bracket so as to apply tension across the joint. Also provided are jigs for use during insertion of pins around joints for orthopedic devices.

7 Claims, 15 Drawing Sheets

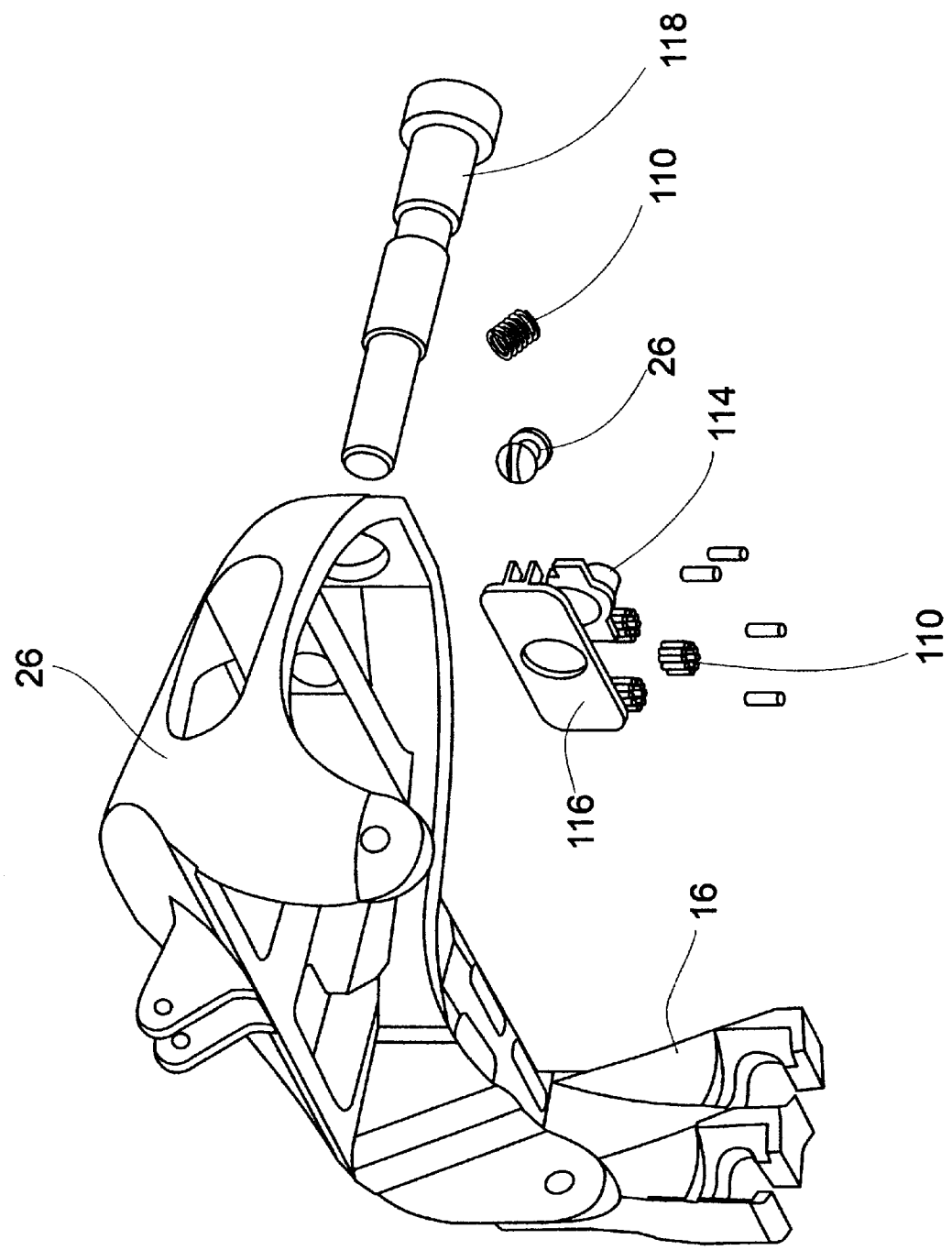

DEVICES FOR PASSIVE MOTION OF JOINTS UNDER TRACTION

This is a continuation-in-part of co-pending U.S. patent application Ser. No. 08/948,362 filed Oct. 10, 1997.

FIELD AND BACKGROUND OF THE INVENTION

The present invention relates to orthopedic surgical devices and, in particular, it concerns devices for moving joints while maintaining traction across the joint.

It is known to employ traction across a joint in the treatment of intra-articular fractures. Especially where the bones are fragmented to an extent which precludes direct surgical procedures to stabilize the fragments, traction is known to induce ligamentotaxis in which the fragments re-align due to forces on their ligamentous and volar plate attachments.

Traction across a fractured joint can be applied by pushing apart pins implanted in each of the adjacent bones. An example of a simple system for applying traction in this manner is the "S Quattro Flexible Mini External Fixator" commercially available from Surgicraft Ltd., England.

It has been found, however, that prolonged application of traction across a fractured joint without movement of the joint frequently results in loss of joint mobility due to irregular re-molding of the joint surfaces and soft tissue scarring (fibrosis). A number of attempts have therefore been made to develop traction systems which permit freedom of movement of the joint, referred to as "dynamic traction" systems.

One approach to dynamic traction is set out in an article entitled "The Dynamic Traction Method: Combining Movement and Traction for Intra-Articular Fractures of the Phalanges" by Robert R. Schenck, MD (*Hand Clinics* 10 (2) May 1994). This describes a system in which rubber bands are mounted between a transosseous wire located in the distal head of the middle phalanx and an external frame. In the primary example, the frame is formed as a large loop in the plane of movement of the joint. The point of connection of the rubber bands can then be slid manually around the loop to flex the joint while maintaining the applied traction. Also discussed are adaptations of existing continuous passive motion devices to apply tension, also by use of rubber bands.

A particular shortcoming of the dynamic traction systems discussed by Schenck is the imprecision and inconvenience of adjustment of the tension applied. Adjustment is achieved primarily by adding or removing rubber bands, thereby giving large discrete jumps in the amount of tension. Although a possibility of twisting the rubber bands is mentioned, no mechanism is provided for such an adjustment. The systems also require professional supervision and demand a high degree of patient compliance and cooperation, making them unsuitable for home-treatment.

A second approach to dynamic traction systems is represented by a proximal interphalangeal joint hinge commercially available under the tradename Compass from Smith & Nephew Richards Inc., USA. This hinge is secured by five pins drilled into the bones. Once positioned, an adjustment screw allows distraction of the joint. Once the desired degree of distraction is achieved, the pin blocks are fixed in position relative to the hinge. It is not possible to achieve a precise and measurable amount of traction. During normal operation of the hinge, no flexibility or elasticity is exhibited.

Although the Compass system provides effectively continuously variable adjustment of the degree of distraction of the joint, the lack of flexibility in the system causes other shortcomings. Firstly, the hinge is extremely sensitive to misalignment. For this reason, a superfluous axial pin is drilled into the bone for alignment of the hinge. However, even with the extra pin, sufficiently precise positioning of the hinge is difficult to achieve. Additionally, even within the operative range of accuracy, a slight misalignment of the hinge may result in a large variation in the distraction of the joint during movement. In such circumstances, the lack of flexibility may cause extreme variations in the force applied to the joint, either in over-traction or compression, potentially resulting in severe damage to the joint. Finally, passive movement of the joint is achieved by labor intensive manual operation of a worm-gear mechanism which demands a high degree of patient compliance.

There is therefore a need for a dynamic traction device for treatment of intra-articular fractures which applies traction elastically across the joint in a manner so as to render slight misalignments non-critical. It would also be advantageous to provide devices for aiding the accurate alignment of such a device.

SUMMARY OF THE INVENTION

The present invention is a dynamic traction device for treatment of conditions such as intra-articular fractures which provides substantially continuous adjustability of traction applied elastically across the joint. Preferred embodiments of the invention allow fully programmable control of a wide range of parameters relating both to the amount of traction applied and the range, speed and frequency of passive movement of the joint, thereby largely avoiding reliance on patient compliance.

According to the teachings of the present invention there is provided, a device for generating passive motion of a joint while applying traction, the joint having been prepared by insertion of at least one pin into each of a proximal and a distal bone adjacent to the joint, the device comprising: (a) a proximal bracket for engaging the at least one pin of the proximal bone; (b) a distal bracket for engaging the at least one pin of the distal bone; and (c) a tension-hinge mechanism connecting between the proximal bracket and the distal bracket, the tension-hinge mechanism including: (i) a hinge for permitting rotational movement of the distal bracket relative to the proximal bracket about a hinge axis, at least one of the proximal bracket and the distal bracket being implemented as a movable bracket slidingly mounted so as to be displaceable in a direction substantially perpendicular to the hinge axis, and (ii) a traction mechanism for applying substantially constant force over a predefined range of positions of the movable bracket so as to apply tension across the joint.

According to a further feature of the present invention, the traction mechanism includes at least one roll-spring.

According to a further feature of the present invention, the traction mechanism includes at least one mechanically-compensated spring.

According to a further feature of the present invention, each of the proximal and the distal brackets is configured for engaging two pins inserted in each of the proximal and distal bones, respectively.

According to a further feature of the present invention, at least one of the proximal and the distal brackets features a high tolerance pin clamp configured to provide at least one angular degree of freedom through a range of at least a few degrees in alignment of the at least one bracket relative to one of the pins.

According to a further feature of the present invention, there is also provided an actuator mechanism mechanically linked between the proximal bracket and the distal bracket for generating relative rotation between the proximal bracket and the distal bracket about the hinge.

According to a further feature of the present invention, the actuator mechanism includes a gear member associated with one of the proximal bracket and the distal bracket and a worm gear mounted rotatably about an axis of rotation associated with the other of the proximal bracket and the distal bracket, the worm gear being engaged with the gear member.

There is also provided according to the teachings of the present invention, a jig for use during insertion of at least one pin into each of a proximal and a distal bone adjacent to a joint prior to attachment of a motion-enabling orthopedic device, the jig comprising a drilling guide bracket including: (a) a proximal jig bracket portion providing at least one drilling guide tube; (b) a distal jig bracket portion providing at least one drilling guide tube; and (c) at least one alignment feature deployed between the proximal and the distal bracket portions and configured to facilitate alignment of at least one part of the drilling guide bracket with the joint.

According to a further feature of the present invention, there is also provided a connector connecting the distal jig bracket portion to the proximal jig bracket portion and configured to allow adjustment of an angle subtended at the at least one alignment feature by the drilling guide tubes of the distal and the proximal jig bracket portions.

According to a further feature of the present invention, the proximal and the distal jig bracket portions and the connector are configured such that the drilling guide tubes define substantially parallel drilling directions.

According to a further feature of the present invention, a major portion of each of the proximal and the distal jig bracket portions is formed from material substantially transparent to X-ray radiation, and wherein the at least one alignment feature includes a positioning element formed at least partially from material readily visible under X-ray imaging techniques.

According to a further feature of the present invention, each of the proximal and the distal jig bracket portions provides at least two drilling guide tubes.

According to a further feature of the present invention, the drilling guide tubes are slidably mounted within the proximal and the distal jig bracket portions to allow adjustment of an extent of projection of each of the drilling guide tubes.

There is also provided according to the teachings of the present invention, a jig for use during insertion of at least one pin into each of a proximal and a distal bone adjacent to a joint prior to attachment of a motion-enabling orthopedic device, the jig comprising a drilling guide block having: (a) at least one proximal drilling guide tube slidably mounted within the guide block to allow adjustment of an extent of projection of the at least one proximal drilling guide tube; (b) at least one distal drilling guide tube slidably mounted within the guide block to allow adjustment of an extent of projection of the at least one distal drilling guide tube; and (c) at least one positioning element formed at least partially from material readily visible under X-ray imaging techniques located between the proximal and the distal drilling guide tubes.

According to a further feature of the present invention, there is also provided a clamp configured for tightening around a region of a limb including the joint so as to immobilize the joint during insertion of pins.

According to a further feature of the present invention, the clamp includes an alignment element formed at least partially from material readily visible under X-ray imaging techniques.

According to a further feature of the present invention, the clamp further includes an adjustment mechanism configured to allow adjustment of a position of the alignment element relative to the joint.

BRIEF DESCRIPTION OF THE DRAWINGS

The invention is herein described, by way of example only, with reference to the accompanying drawings, wherein:

FIG. 8 is an exploded isometric view of the device of FIG. 4A;

DESCRIPTION OF THE PREFERRED EMBODIMENTS

The present invention is a dynamic traction device. The device is useful for treatment of a range of conditions such as intra-articular fractures and any other pathological or post-operative condition (arthroplaty) in which traction and/or early passive motion of the joints is indicated.

The principles and operation of devices according to the present invention may be better understood with reference to the drawings and the accompanying description.

Figure 1:
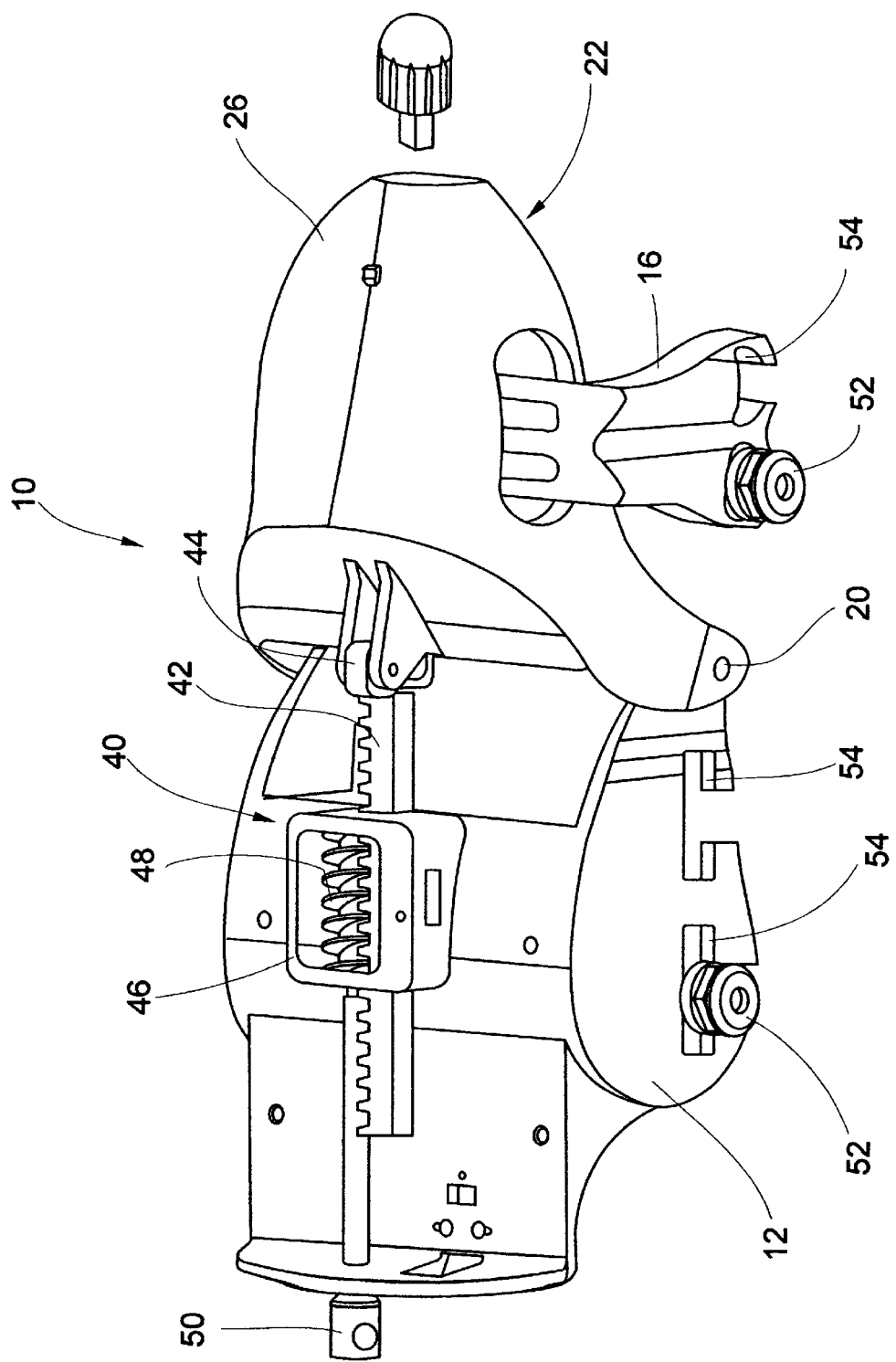
FIG. 1 is a first isometric view of a dynamic traction device, constructed and operative according to the teachings of the present invention, for use in surgical treatment of conditions such as intra-articular fractures in a wrist joint.
Figure 2:
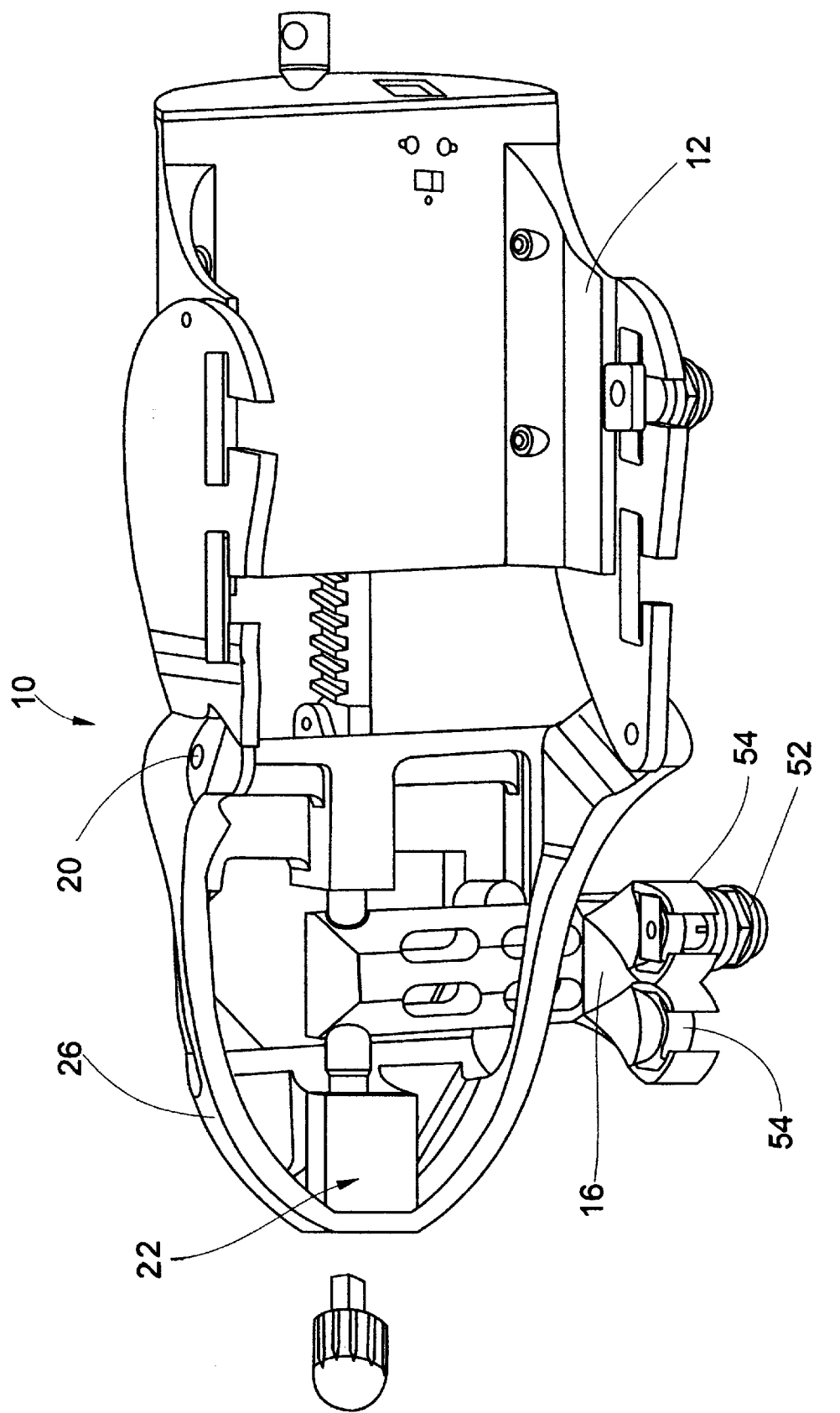
FIG. 2 is second isometric view of the device of FIG. 1.
Figure 3:
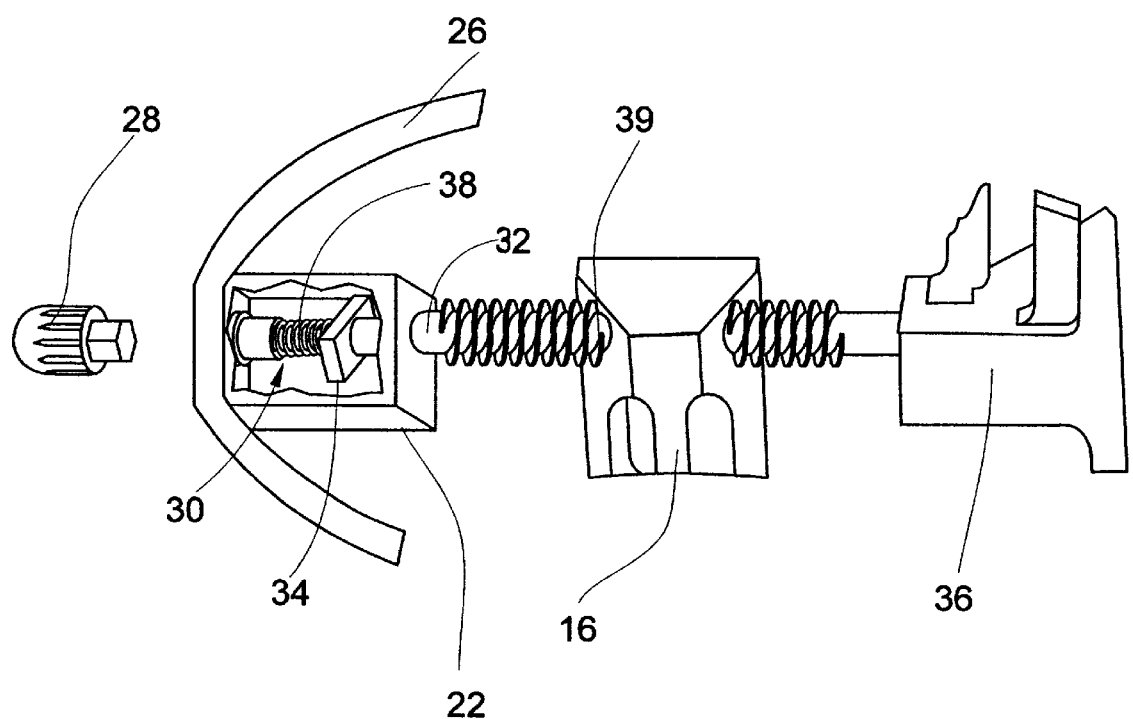
FIG. 3 is a partial isometric cut-away view of the device of FIG. 1 showing a variable-force spring assembly.

Referring now to the drawings, FIGS. 1–3 show a device, generally designated 10, for generating passive motion of a joint while applying traction. This device is generally parallel to that described in copending U.S. patent application Ser. No. 08/948,362, and parallel co-pending International Application Ser. No. PCT/US98/14748, (both unpublished on the date of filing of this application) which are hereby incorporated by reference as if fully set out herein.

Generally speaking, device 10 has a proximal bracket 12 for engaging pins drilled into a proximal bone adjacent to tie joint, and a distal bracket 16 for engaging pins drilled into a distal bone adjacent to the joint. Brackets 12 and 16 are connected by a tension-hinge mechanism which includes a hinge 20 for permitting relative rotational movement of the brackets, and a traction mechanism 22. Traction mechanism 22, as described in the aforementioned applications, is configured to progressively deform a spring element so as to allow substantially continuous adjustment of the tension applied elastically across the joint.

Although device 10 can be used with minor adaptations for a wide range of different joints, the particular example shown here is designed for use with a wrist joint.

It is a preferred feature of most embodiments of the present invention that most or all of the device is produced from X-ray transparent materials to allow imaging of the injured joint while the device is in place. A range of suitable plastics and other polymer materials generally known in the art may be used.

Turning now to the features of device 10 in more detail, a preferred implementation of the tension-hinge mechanism is best seen in the cut-away view of FIG. 3. In this case, the major distal portion 26 of device 10 is connected at rigid hinges 20 to proximal bracket 12. The relatively small distal bracket 16 which directly engages the distal pins is attached to distal portion 26 by an adjustable spring-loaded mounting 30. Specifically, spring-loaded mounting 30 includes a partially-threaded adjustment rod 32 which is aligned within bores through two support blocks 34, 36 so as to be free to slide axially. Rod 32 is biased by an elastic element, preferably a helical spring 38 towards a distally displaced resting position. Bracket 16 has a threaded inner bore 39 within which a threaded part of rod 32 is engaged. Thus rotation of rod 32 by means of an adjuster 28 either adjusts the position of bracket 16 between the two support blocks or, if bracket 16 is held still, adjusts the tensile force exerted on bracket 16 by spring 38. Preferably, adjuster 28 is configured as a removable key to prevent unauthorized adjustment of the device after it is positioned.

Device 10 preferably also provides an actuator mechanism 40 mechanically linked between proximal bracket 12 and distal bracket 16 for generating relative rotation between proximal bracket 12 and distal bracket 16 about hinge 20. This allows application of passive motion therapy while maintaining traction across a joint. In a preferred implementation, actuator mechanism 40 includes a toothed rack 42 driven by a worm gear 48. In the case illustrated here, rack 42 is pivotally linked to distal portion 26 through a linkage 44 while worm gear 48 is deployed in a housing 46 attached to bracket 12. In order to allow use of a straight rack 42, linkage 44 is preferably implemented as a pin-and-slot coupling to accommodate the range of alignment occurring during flexing of the device about hinge 20.

Preferably, worm gear 48 is driven via a coupling 50 through a flexible drive cable by a portable control unit which can be strapped to the arm of a patient (not shown). The control unit typically includes an electric motor driven from batteries under the control of a programmable microprocessor unit. This allows a surgeon to set and modify parameters of a passive exercise treatment program, including the extent and speed of rotation about an axis of rotation, the delay between successive movements, the length of each treatment session and the time between sessions. All of these parameters may be programmed to change progressively or in steps during the course of the treatment.

Optionally, the control unit may include a connection device, preferably in the form of a modem or tone-dialing connection to a telephone network, configured to form a connection with a central reprogramming station. This allows adjustment or reprogramming of the parameters of the treatment program within a home-care program without requiring the patient to attend a hospital or clinic.

In an alternative implementation, worm gear 48 may be manually operated to achieve passive movement of the joint.

As mentioned above, device 10 is skeletally anchored by pins which are inserted into a proximal and a distal bone adjacent to the damaged joint. In preferred implementations, it has been found valuable to employ two fixation pins to positively align the bone on each side of the joint. To this end, at least one and preferably both of the proximal and distal brackets 12 and 16 are configured for engaging two pins inserted in the corresponding bones.

Preferably, some or all of the pins are received by high tolerance pin clamps configured to provide at least one degree of freedom of adjustment. This makes the precision of positioning of the fixation pins less critical and renders attachment of the device particularly easy. Linearly, adjustment of at least a few millimeters is readily achieved by mounting one or more pin using a flanged clamping sleeve 52 located within a slot 54.

At least some of the high tolerance pin clamps are preferably configured to provide at least one angular degree of freedom through a range of at least several degrees, and preferably, at least about 10°, in alignment of the pins relative to the bracket. This is achieved by providing curved surfaces around slot 54 and correspondingly curved abutment surfaces of sleeve 52 as shown here on distal bracket 16 as best viewed in FIG. 2.

Although the device of FIGS. 1–3 provides considerable advantages over the prior art references described above, it does not provide a complete solution. Specifically, while the elasticity of the adjustment renders the precise location of hinge 20 less critical, it has been found that slight misalignments taken up by the spring elements may cause major variations in the traction applied across the joint during flexing. Major variations in the applied traction may render the device much less effective and could possibly be dangerous.

To address these problems, it is a particular feature of most highly preferred implementations of the present invention that device 10 is provided with a traction mechanism configured to apply substantially constant force over a predefined range of positions of the brackets. This allows the traction mechanism to take up any small displacements resulting from misalignment of the hinge position without adversely affecting operation of the device.

It should be appreciated in this context that the phrase "substantially constant force" is used to refer to any case in which the behavior of a spring system more closely resembles a constant force than a Hooke's law linear variation over a given range of movement. This may be achieved either by use of a spring system which inherently generates constant or near-constant force, or by modifying the effect of a non-constant-force spring through its mechanical deployment and/or use of additional components to compensate at least partially for variations in force resulting from the state of the spring. An example of the former will now be described with reference to FIGS. 4–6 while the latter will be exemplified with reference to FIGS. 7–9.

Figure 4:
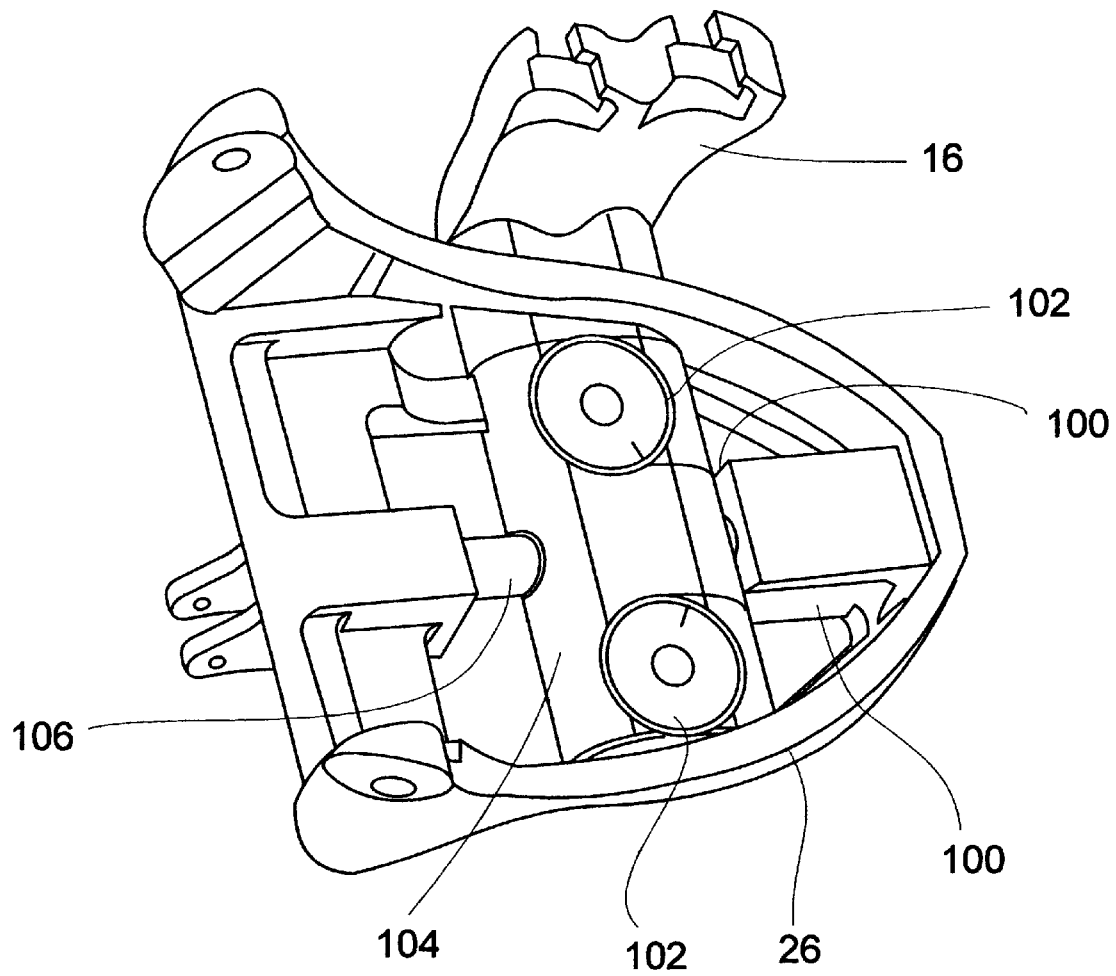
FIG. 4 is a partial isometric view of a first variant of the device of FIG. 1 employing a first constant-force spring assembly.
Figure 5:
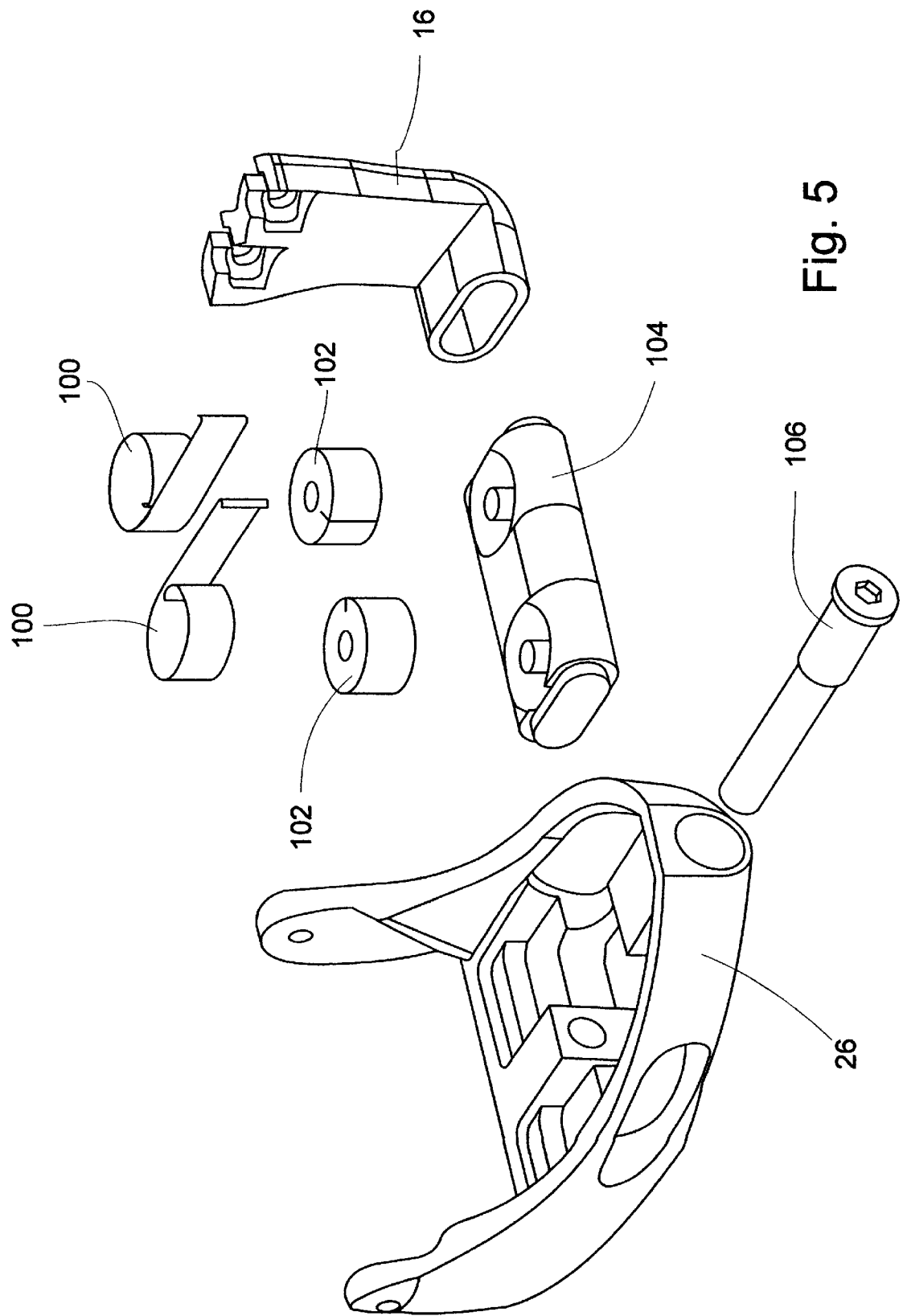
FIG. 5 is an exploded isometric view of the device FIG. 4.
Figure 6:
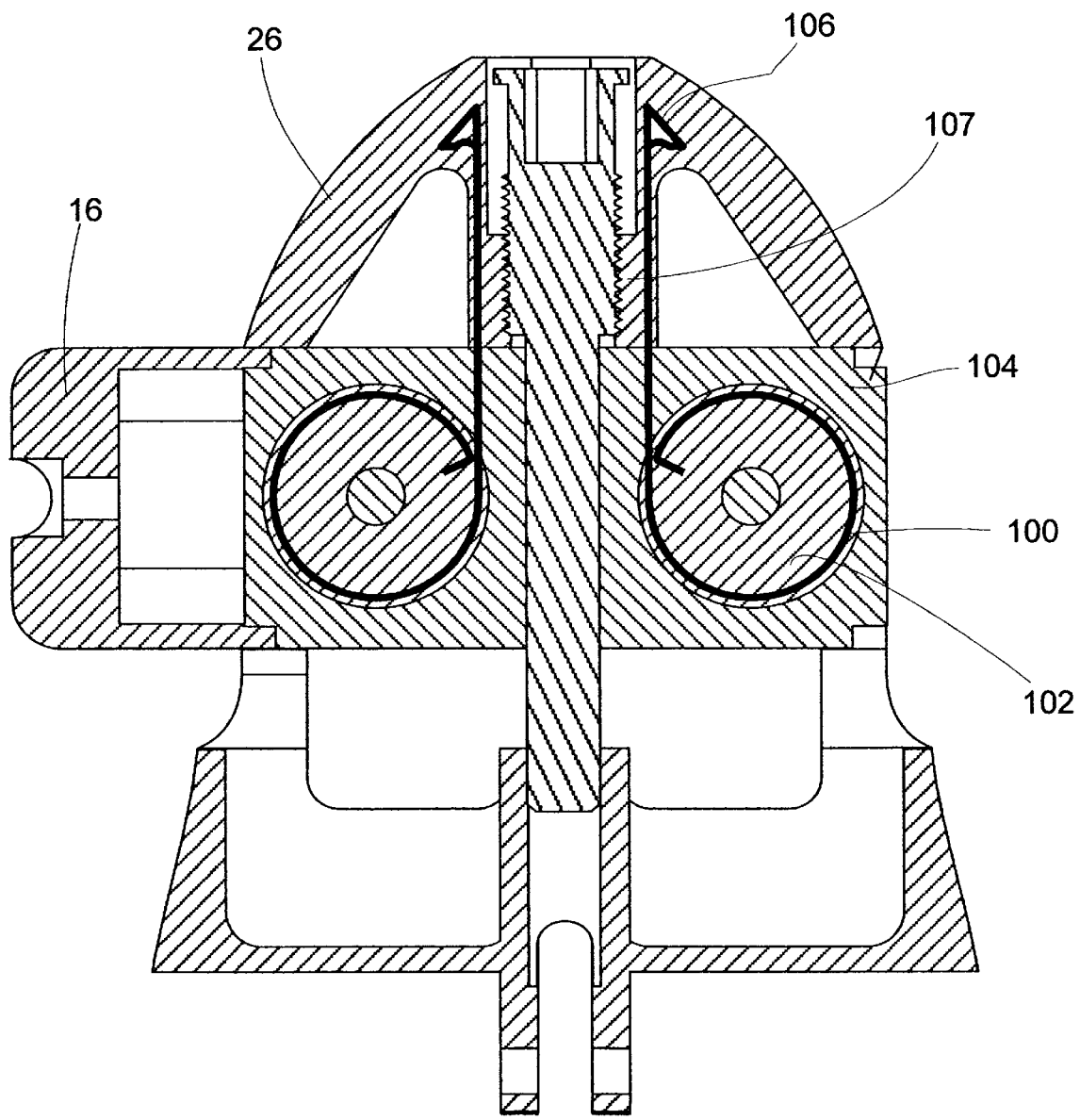
FIG. 6 is a cross-sectional view taken through the device FIG. 4.

Turning now to FIGS. 4–6, there is shown a variant of device 10 in which the traction mechanism is implemented using a number of roll-springs 100. As seen in FIG. 5, each roll-spring 100 is a metallic strip which is formed with an inherent curvature so as to tend to roll onto itself. Each strip is wound about a rotatable drum 102 and may be pulled so as to progressively unwind the strip from the drum. This structure is known to provide a close approximation to a constant spring force over a considerable range of movement.

In one particularly convenient implementation, drums 102 and roll-springs 100 are mounted within a cartridge 104 which may be connected as part of distal bracket 16. A rod 106 passes through cartridge 104 so as to delimit the direction of allowed relative motion between brackets 12 and 16. In this case, however, rod 106 does not provide any adjustment feature since the applied force remains substantially constant so long as the roll-springs are within their range of movement and bracket 16 does not become mechanically obstructed by the ends of the openings through distal portion 26 through which it passes. Adjustment of the traction force, when required, may be achieved either by changing the number of roll-springs operating, or by swapping the roll-springs for alternative roll-springs of different strengths.

In order to position bracket 16 correctly during deployment of the device, rod 106 may optionally provide an adjustable displacement mechanism for temporarily holding bracket 16 in position. This option is illustrated in FIG. 6. Specifically, an enlarged forward part of rod 106 is shown in threaded engagement with an internally threaded housing 107 such that, by turning rod 106, cartridge 104 is pushed rearwards (i.e., towards hinge 20) against springs 100. Once the device is deployed on the pins, rod 106 is turned so as to retract it to a withdrawn position as shown, thereby freeing springs 100 to function as described.

Figure 7B:
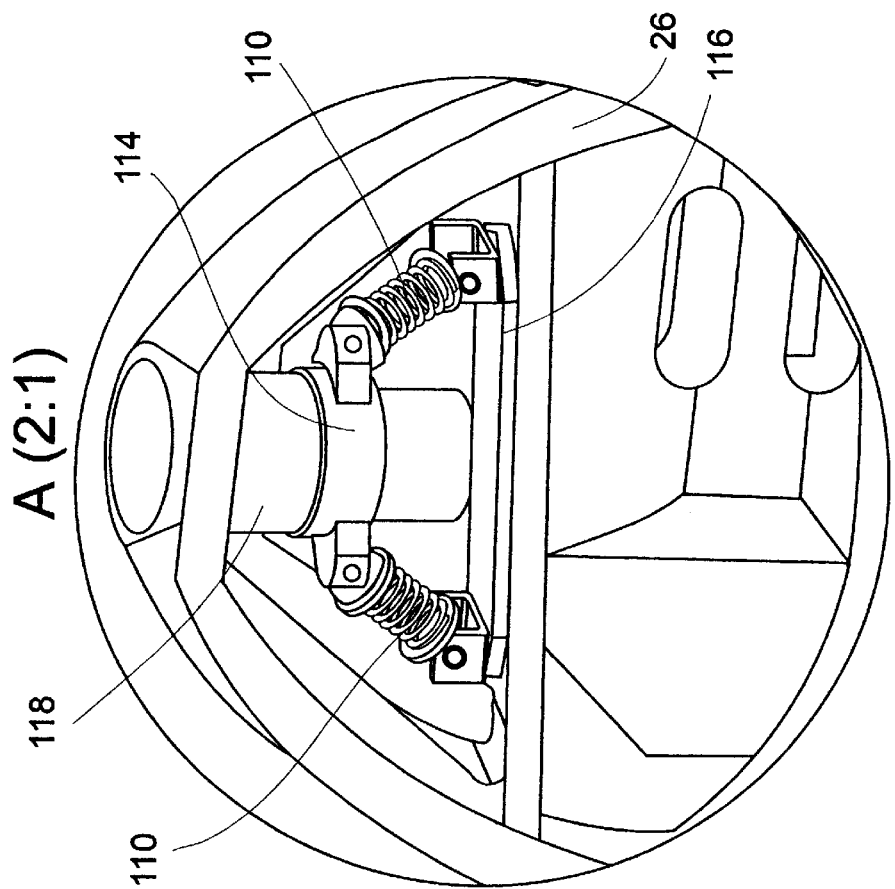
FIG. 7B is an enlarged view of the region of FIG. 7A designated "A"
Figure 7A:
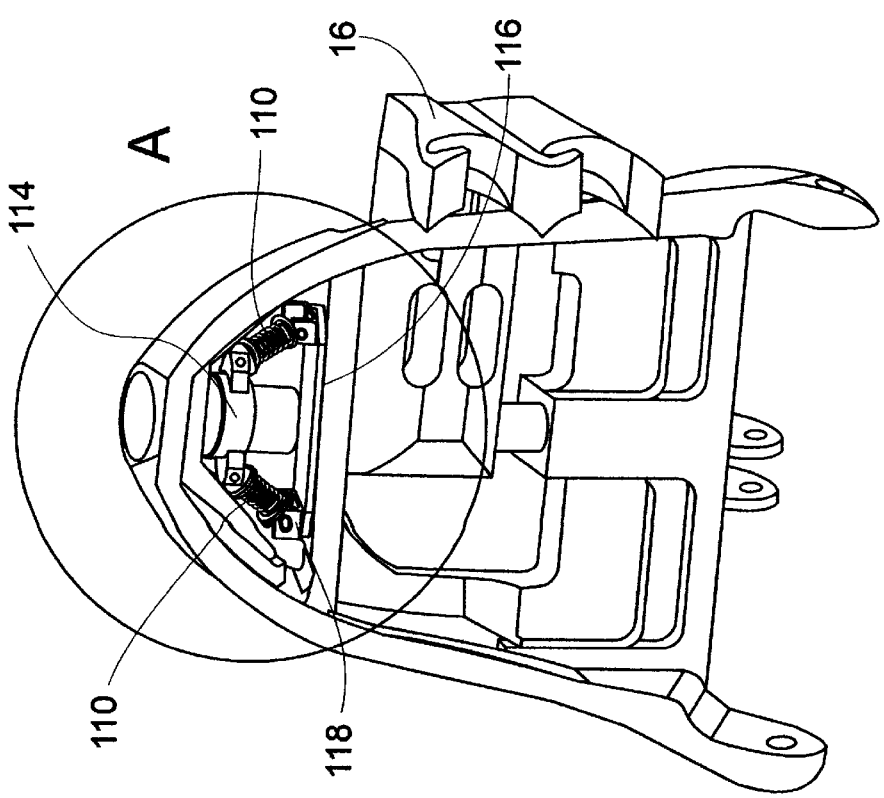
FIG. 7A is a partial isometric view of a second variant of the device of FIG. 1 employing a second constant-force spring assembly.

Turning now to FIGS. 7–9, these show second and third variants of device 10 in which the traction mechanism is implemented using a number of mechanically-compensated springs. Specifically, in the second variant illustrated in FIGS. 7A, 7B and 8, the traction mechanism shown employs two conventional helical compression springs 110 each deployed at a variable inclination to the direction of motion between a yoke 114 and an abutment surface 116 rigidly attached to, or integrally formed with, distal portion 26. Yoke 114 is mechanically coupled to distal bracket 16 through a partially-threaded rod 118. A variable component of the force of springs 110 acts along the direction of relative motion between distal bracket 16 and distal portion 26 varying as the cosine of the angle between the direction of the springs and the direction of motion. This angle becomes greater as the spring is compressed, thereby to a large extent offsetting the increased force exerted by the springs.

Although only providing a rather rough approximation to "constant force" characteristics, this implementation of the traction mechanism is particularly compact and can provide relatively large traction forces. The mechanism does, however, suffer from a limited range of movement. This is preferably addressed by providing screw adjustment via rod 118 to ensure that the traction mechanism is initially near the middle of its range of motion when the device is deployed.

Figure 9B:
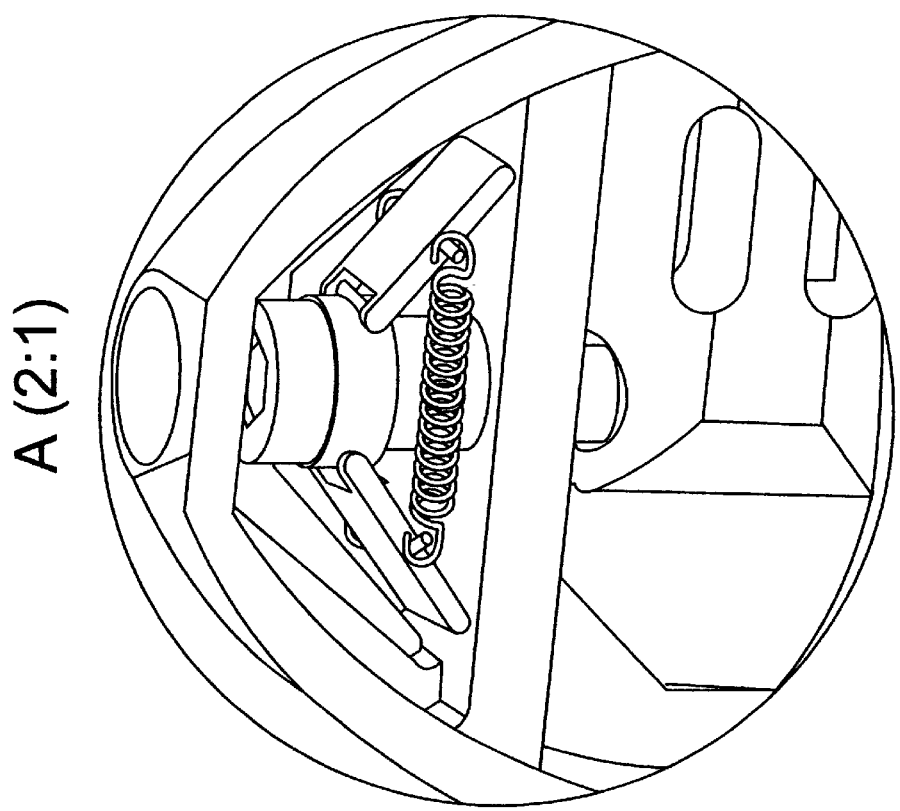
FIG. 9B is an enlarged view of the region of FIG. 9A designated "A"
Figure 9A:
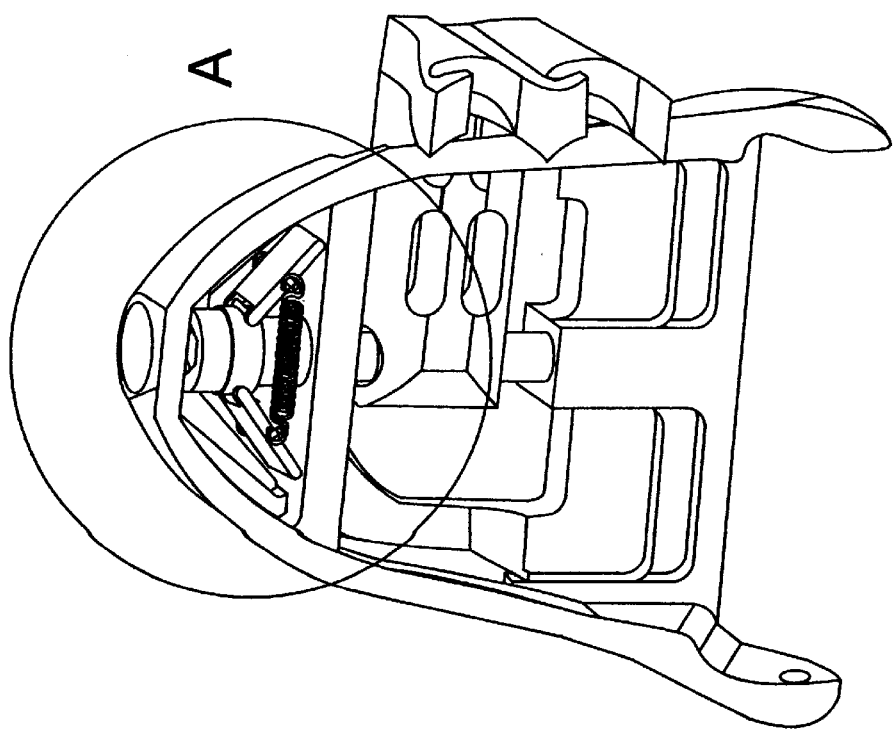
FIG. 9A is a partial isometric view of a third variant of the device of FIG. 1 employing a third constant-force spring assembly.

Turning now to FIGS. 9A and 9B, there is shown a further variant in which two conventional helical springs 110, deployed transverse to the direction of relative motion, act on two lever flaps 112 which are pivotally connected to yoke 114. This structure results in a variable component of the springs' forces being transferred to abutment surface 116 in such a way as to somewhat offset the Hooke's law variation of tension in the springs themselves.

Figure 10:
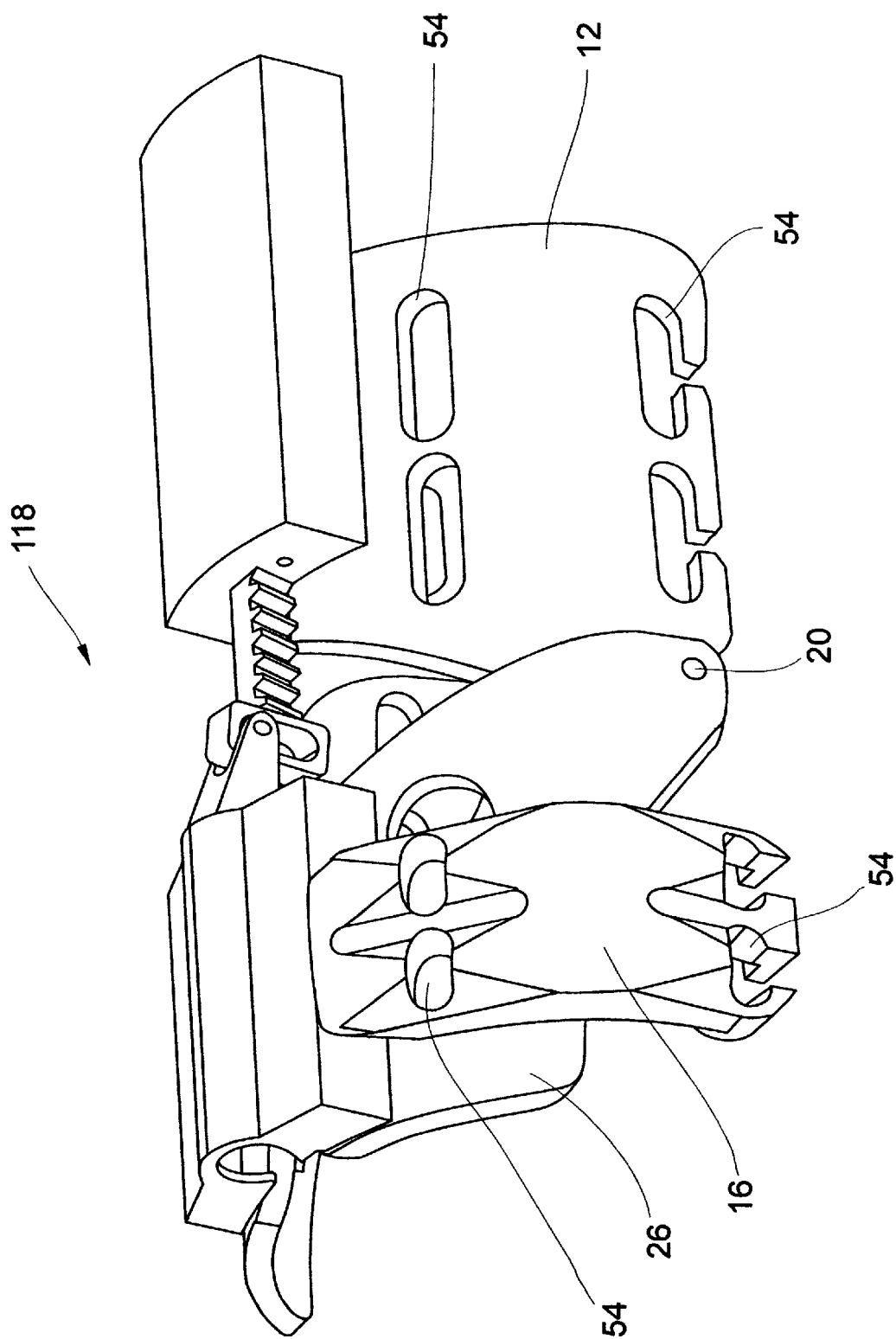
FIG. 10 first isometric view of a dynamic traction device, constructed and operative according to the teachings of the present invention, providing multiple mounting orientations.
Figure 11:
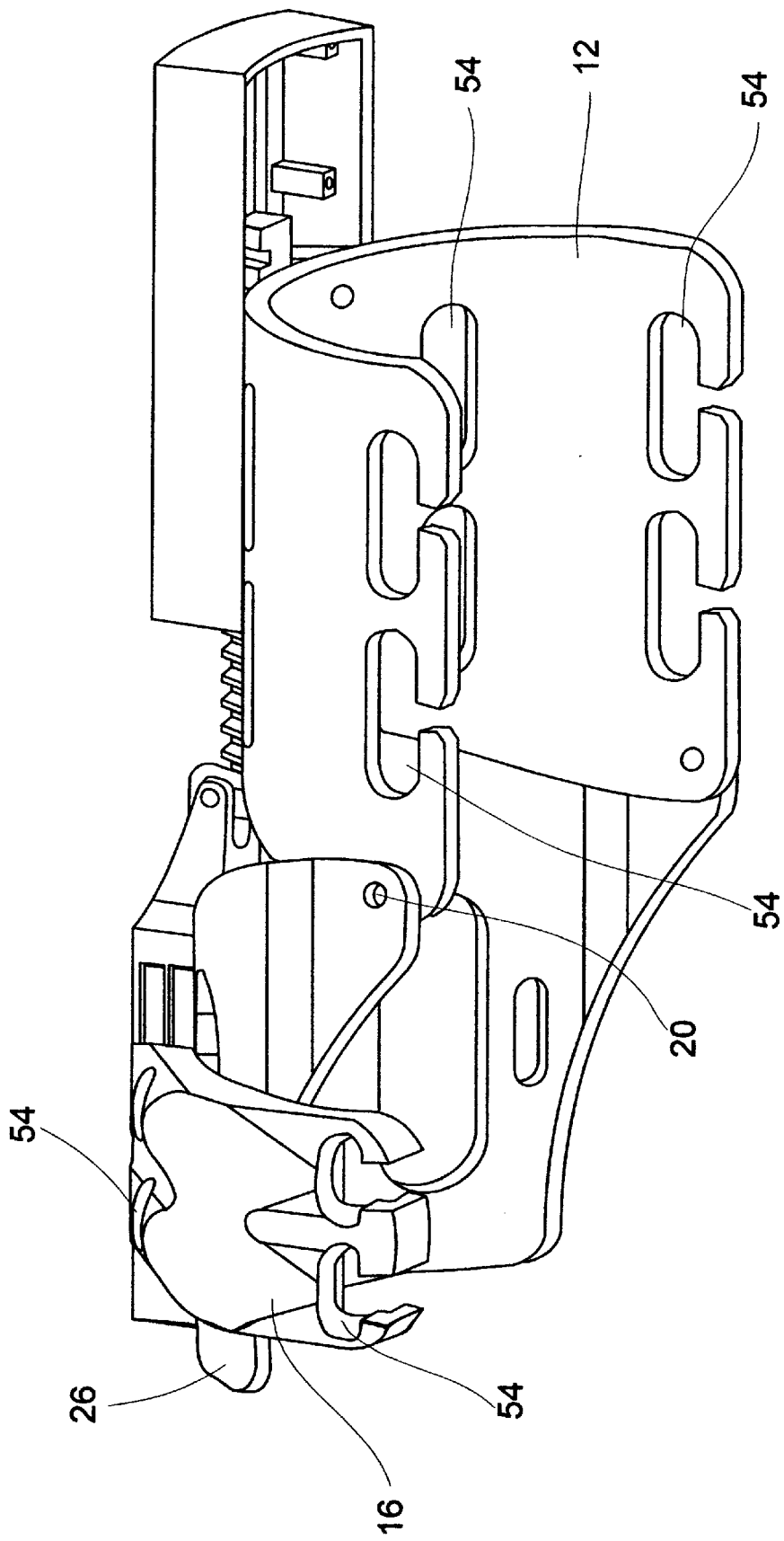
FIG. 11 is second isometric view of the device of FIG. 10.

Referring now briefly to FIGS. 10 and 11, there is shown a variant implementation of device 10, generally designated 118. Device 118 is generally similar to device 10 except that each of brackets 12 and 16 is formed with at least two sets of slots 54 configured for clamping pins at different angles relative to hinge 20. It has been found that, in certain cases, it is desirable to generate flexing motion of the joint in directions other than the flexion and extension (up-down) motion provided by device 10. Clearly, individual devices according to the principles of the present invention could be designed for each intended application. However, device 118 provides a more convenient and economical solution by allowing the use of a single device for motion in more than one direction.

Turning now to further aspects of the present invention, the present invention also preferably provides a jig to facilitate accurate drilling during insertion of at least one pin into each of a proximal and a distal bone adjacent to a joint prior to attachment of a motion-enabling orthopedic device. While the jig may be used to advantage with a wide range of different motion-enabling orthopedic devices, it is believed to be particularly valuable when used in combination with a device constructed and operative according to the principles of the present invention described above and in the above-incorporated applications.

Features of the jig of the present invention will now be described with reference to two preferred examples. The first, intended primarily for a larger joint such as a wrist or elbow, will be described with reference to FIGS. 12 and 13, while the second, particularly suited to a smaller joint such as an inter-phalangeal joint, will be described with reference to FIGS. 14 and 15.

Figure 12:
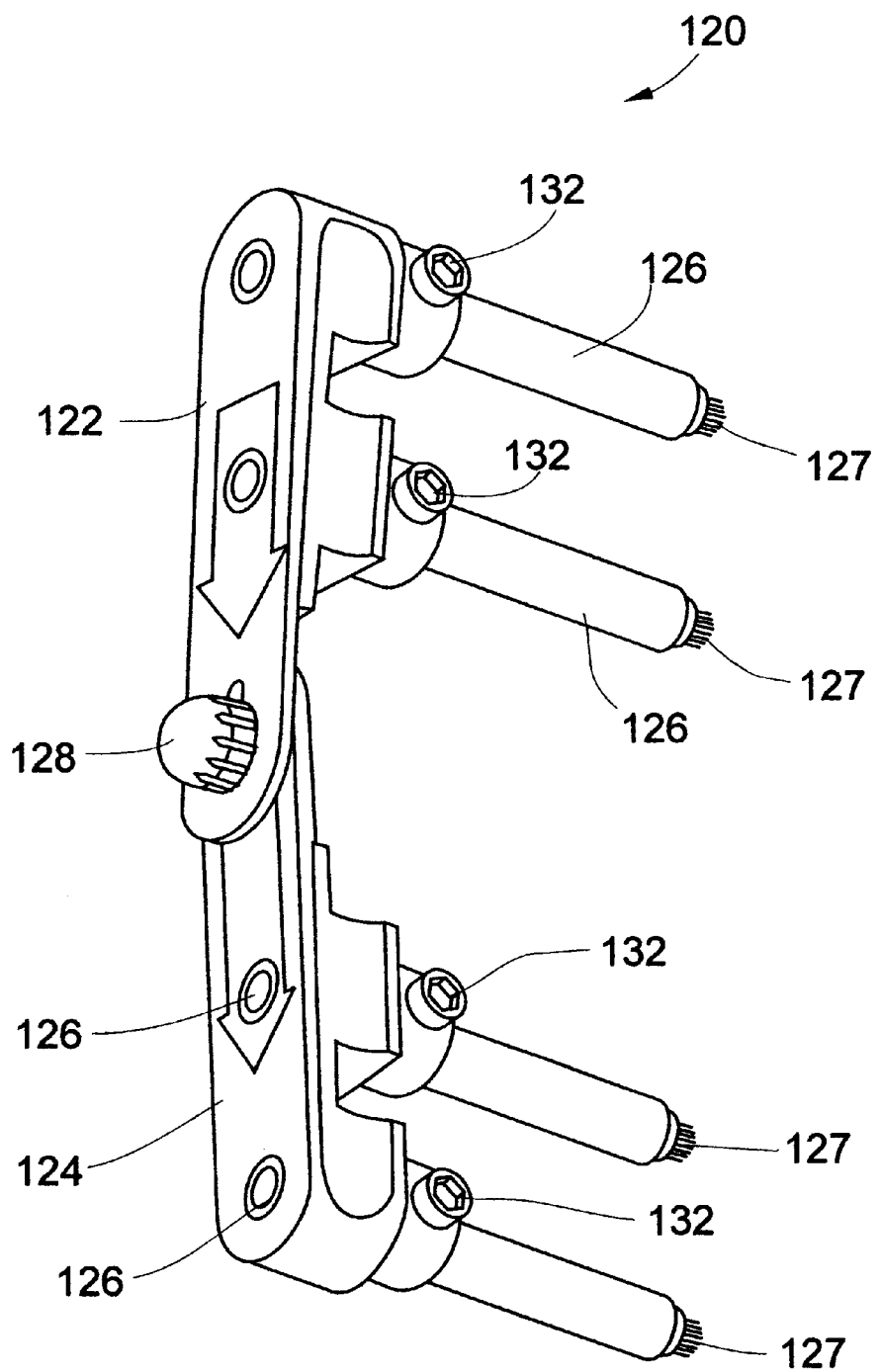
FIG. 12 is an isometric view of a jig for use during insertion of pins for orthopedic clamping such as using the devices of FIGS. 1–11.
Figure 13:
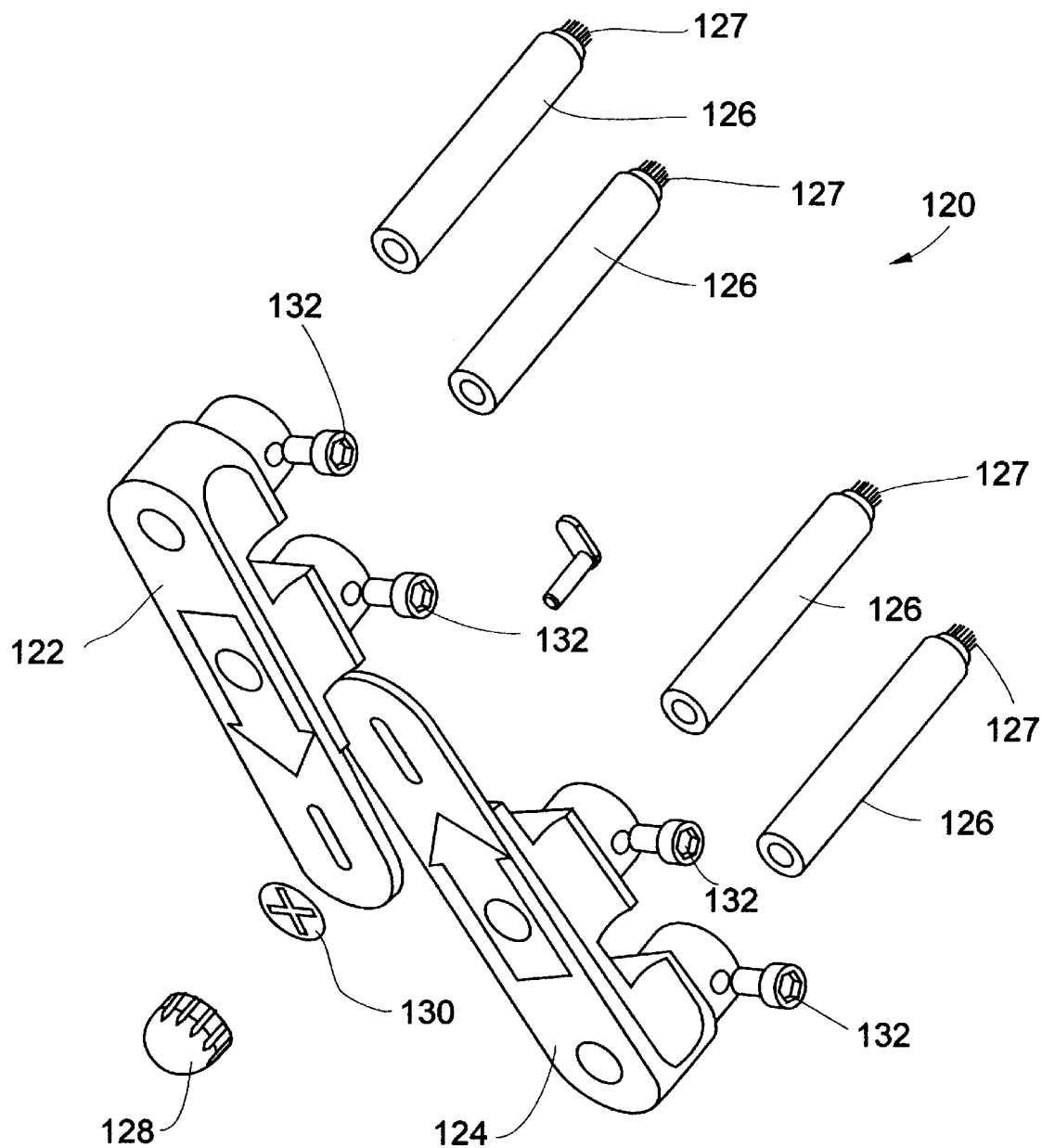
FIG. 13 is an exploded isometric view of the jig of FIG. 12.

Turning now to FIGS. 12 and 13, there is shown a jig implemented as a drilling guide bracket 120. In this case, the drilling guide bracket is made up of separate proximal and distal jig bracket portions 122 and 124, each providing at least one, and preferably two, drilling guide tubes 126. The bracket portions are attached by a connector 128 which is configured to allow adjustment of the angle between them. Connector 128 is preferably associated with slots in one or both of proximal and distal jig bracket portions 122 and 124 to allow some degree of adjustability of the distance between the connector and the drilling guide tubes.

Preferably, drilling guide bracket 120 includes at least one alignment feature 130 deployed between the proximal and the distal bracket portions, preferably at or aligned with connector 128, and configured to facilitate alignment of at least one part of the drilling guide bracket with the joint. Preferably, alignment feature 130 is implemented as an element which is readily visible under some real-time or near-real-time medical imaging technique such that it can be used by a surgeon to align the bracket correctly relative to the joint. Examples include elements which are either partially opaque or particularly reflective to appropriate types of radiant energy such as X-ray or ultrasound. In the preferred example illustrated here, alignment feature is implemented as a metallic shaped washer associated with connector 128 and shaped to provide an easily identifiable center under X-ray imaging techniques. The major portion of each of the proximal and the distal jig bracket portions is correspondingly formed from material substantially transparent to X-ray radiation, while drilling guide tubes 126, themselves, are typically made from metallic material, preferably stainless steal, which is also readily visible under X-ray.

The proximal and the distal jig bracket portions 122 and 124 and connector 128 are preferably configured such that drilling guide tubes 126 define substantially parallel drilling directions. Tubes 126 are preferably slidably mounted within proximal and distal jig bracket portions 122 and 124 to allow adjustment of the extent to which each of the drilling guide tubes projects. This allows alignment of the tubes to conform to the contour of the body so that they each contact the surface of the skin prior to drilling. Once correctly aligned, they are fixed in position by tightening clamping screws 132. Each drilling guide tube preferably features a plurality of sharp end features 127 to ensure positive location of the guide tubes against the skin prior to drilling.

Figure 14:
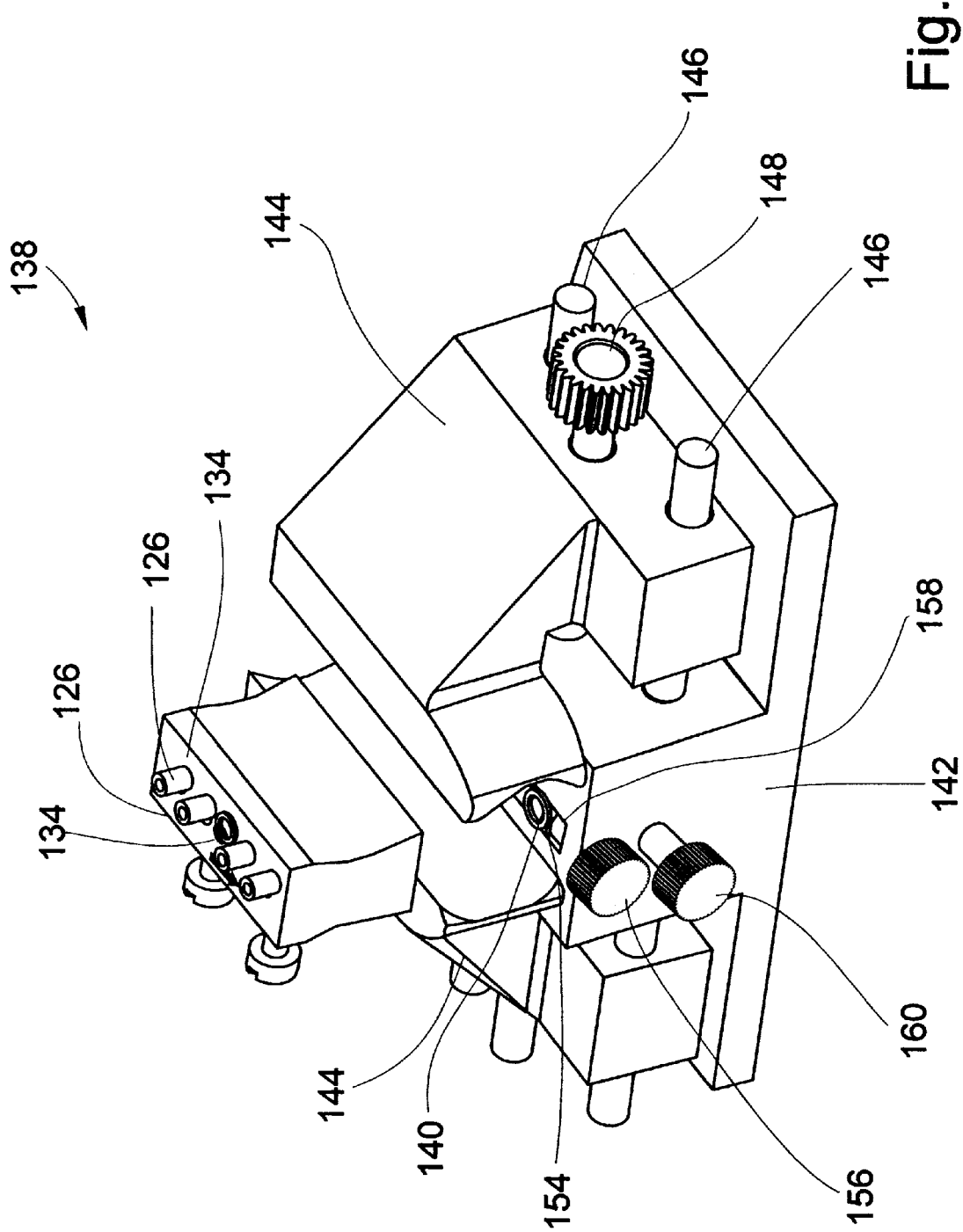
FIG. 14 is an isometric view of a jig for use during insertion of pins for orthopedic clamping of a finger.
Figure 15:
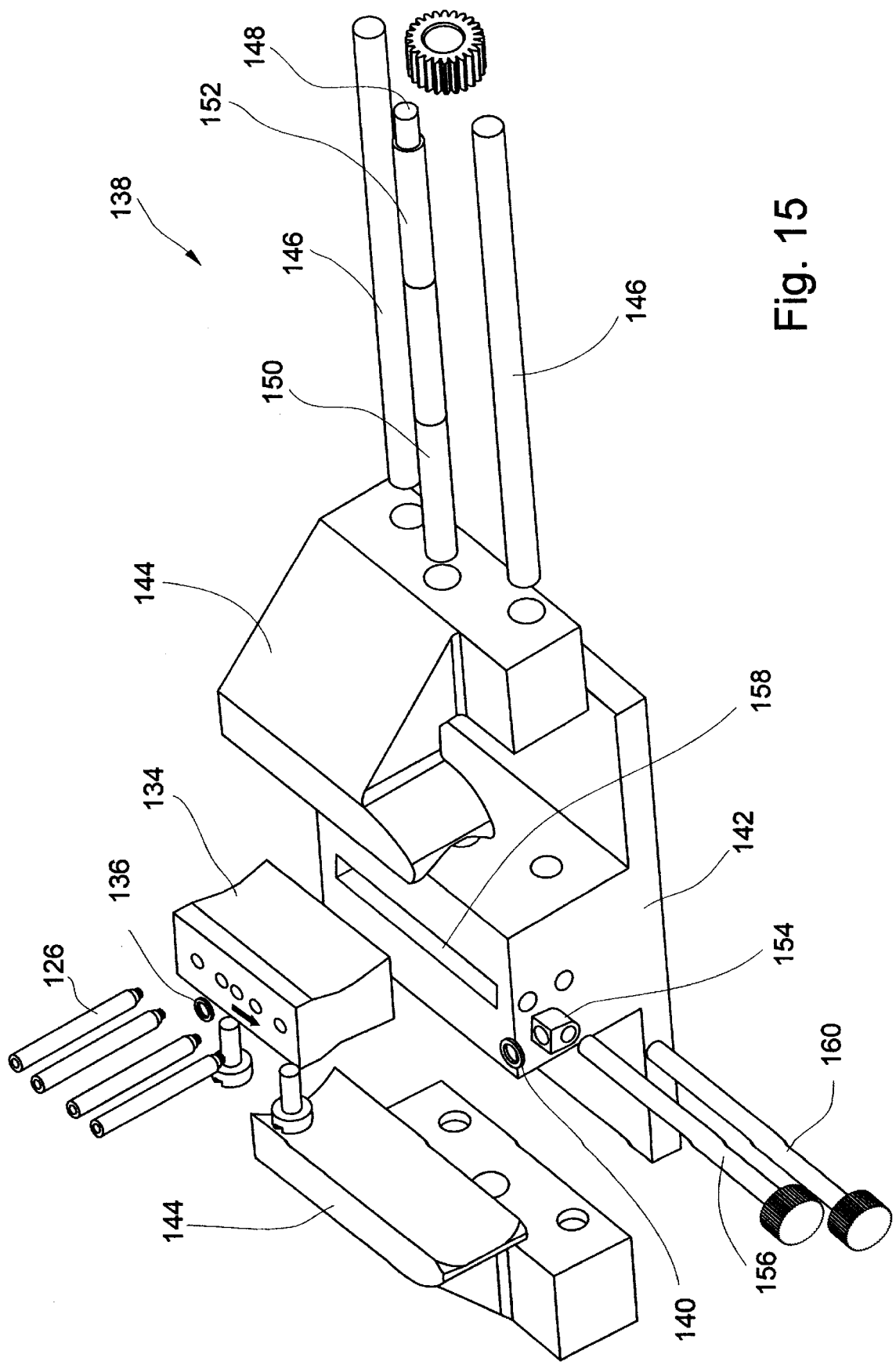
FIG. 15 is an exploded isometric view of the jig of FIG. 14.

Turning now to FIGS. 14 and 15, there is shown a second jig including a drilling guide bracket, in this case featuring proximal and distal jig bracket portions formed as part of a drilling guide block 134. As with drilling guide bracket 120, drilling guide block 134 includes at least one, and preferably two, proximal drilling guide tubes 126 and at least one, and preferably two, distal drilling guide tubes 126, preferably slidably mounted, within the proximal and distal portions of guide block 134, respectively. At least one positioning element 136 formed at least partially from material readily visible under X-ray imaging techniques is located between the proximal and the distal drilling guide tubes.

As an alternative to the articulated construction of drilling guide bracket 120, this jig preferably supplements drilling guide block 134 with a clamp 138 configured for tightening around a region of a limb including the joint so as to straighten and immobilize the joint during insertion of the pins.

Preferably, clamp 138 includes an alignment element 140 formed at least partially from material readily visible under X-ray imaging techniques, and an adjustment mechanism configured to allow adjustment of a position of alignment element 140 relative to the joint.

Referring to the example illustrated here in more detail, clamp 138 is here formed from a base 142 with two lateral clamping jaws 144 which open and close by sliding along two guide rods 146 under control of a threaded actuator rod 148. To provide more efficient and symmetrical clamping action, actuator rod 148 preferably features counter-threaded portions 150 and 152 which engage correspondingly threaded bores in jaws 144.

The adjustment mechanism for alignment element 140 is here implemented as a slide 154 mounted on a threaded adjustment rod 156 within a slot 158 in base 142. Additionally, the assembly of clamping jaws 144 and actuator rod 148 is free to slide relative to base 142 in a direction perpendicular to slot 158 until actuator rod 148 is locked by a lateral bolt 160. Thus, by moving clamping jaws 144 relative to base 142 and turning adjustment rod 156, the position of alignment element 140 can be adjusted in two dimensions until it lies in direct alignment with the desired part of the joint as viewed by X-ray. By then positioning drilling guide block 134 with positioning element 136 aligned with both the joint and alignment element 140, a high degree of precision can readily be achieved.

The inventors have found the preference of surgeons consulted to-date to be an implementation in which drilling guide block 134 and clamp 138 are mechanically independent, thereby leaving a large degree of control in the hands of the surgeon. However, alternative and possibly preferred implementations may readily be constructed in which drilling guide block 134 is mechanically linked to clamp 138 so as to allow controlled adjustment of their relative positions while maintaining certain aspects of alignment therebetween.

It will be appreciated that the above descriptions are intended only to serve as examples, and that many other embodiments are possible within the spirit and the scope of the present invention.

What is claimed is:

1. A device for generating passive motion of a joint while applying traction, the joint having been prepared by insertion of at least one pin into each of a proximal and a distal bone adjacent to the joint, the device comprising:

(a) a proximal bracket for engaging the at least one pin of the proximal bone;
   (b) a distal bracket for engaging the at least one pin of the distal bone; and
   (c) a tension-hinge mechanism connecting between said proximal bracket and said distal bracket, said tension-hinge mechanism including:
      (i) a hinge for permitting rotational movement of said distal bracket relative to said proximal bracket about a hinge axis, at least one of said proximal bracket and said distal bracket being implemented as a movable bracket slidingly mounted so as to be displaceable in a direction substantially perpendicular to said hinge axis, and
      (ii) a traction mechanism having an elastic element for applying substantially constant force over a predefined range of positions of said movable bracket so as to apply tension across the joint.

2. The device of claim 1, wherein said elastic element includes at least one roll-spring.

3. The device of claim 1, wherein said elastic element includes at least one mechanically-compensated spring.

4. The device of claim 1, wherein each of said proximal and said distal brackets is configured for engaging two pins inserted in each of the proximal and distal bones, respectively.

5. The device of claim 1, wherein at least one of said proximal and said distal brackets features a high tolerance pin clamp configured to provide at least one angular degree of freedom through a range of at least a few degrees in alignment of said at least one bracket relative to one of the pins.

6. The device of claim 1, further comprising an actuator mechanism mechanically linked between said proximal bracket and said distal bracket for generating relative rotation between said proximal bracket and said distal bracket about said hinge.

7. The device of claim 6, wherein said actuator mechanism includes a gear member associated with one of said proximal bracket and said distal bracket and a worm gear mounted rotatably about an axis of rotation associated with the other of said proximal bracket and said distal bracket, said worm gear being engaged with said gear member.

* * * * *